(12) United States Patent
Johnson (10) Patent No.: US 10,610,620 B2
(45) Date of Patent: Apr. 7, 2020

(54) METHOD AND DEVICES FOR PREVENTING RESTENOSIS IN CARDIOVASCULAR STENTS

(75) Inventor: Alfred David Johnson, San Leandro, CA (US)

(73) Assignee: Monarch Biosciences, Inc., Los Angeles, CA (US)

(*) Notice: Subject to any disclaimer, the term of this patent is extended or adjusted under 35 U.S.C. 154(b) by 159 days.

(21) Appl. No.: 13/220,522

(22) Filed: Aug. 29, 2011

(65) Prior Publication Data

US 2011/0313513 A1     Dec. 22, 2011

Related U.S. Application Data

(62) Division of application No. 12/182,119, filed on Jul. 29, 2008, now Pat. No. 8,007,674.

(60) Provisional application No. 60/952,818, filed on Jul. 30, 2007.

(51) Int. Cl.
   *A61F 2/82*   (2013.01)
   *A61L 31/02*  (2006.01)
   *A61L 31/14*  (2006.01)

(52) U.S. Cl.
   CPC ............ *A61L 31/022* (2013.01); *A61L 31/14* (2013.01); *A61F 2/82* (2013.01); *A61L 2400/12* (2013.01); *Y10T 428/198* (2015.01)

(58) Field of Classification Search
   CPC .... A61F 2002/30092; A61F 2210/0014; A61F 2310/00389; A61F 2310/00023; A61F 2/82; A61F 2310/00407; A61F 2250/0036; A61L 31/022; A61L 31/14; A61L 2400/12; Y10T 428/195; Y10T 428/198; Y10S 977/712; B32B 3/30; B32B 3/02; B32B 15/01; B32B 15/04; B32B 15/043; G03F 2009/005; G03F 9/70; G03F 7/094; B81C 2201/0156; B81C 2201/0159; B81C 1/00396; C21D 2251/00; H01L 21/0332; H01L 21/3081; H01L 2224/03474; H01L 2227/11474; H01L 2224/27472; H01L 2224/27474; C23C 28/02
   USPC .......... 623/1.13, 1.46; 216/72; 428/550, 596
   See application file for complete search history.

(56) References Cited

U.S. PATENT DOCUMENTS

| 368,425 A | 8/1887 | Ross et al. |
| 538,593 A | 4/1895 | Naylor, Jr. |
| 1,560,335 A | 11/1925 | Czochralski |

(Continued)

FOREIGN PATENT DOCUMENTS

| EP | 0053596 | 6/1982 |
| EP | 0310439 | 4/1989 |

(Continued)

OTHER PUBLICATIONS

Johnson, David et al.; U.S. Appl. No. 11/006,501 entitled "Anastomosis device and method," filed Dec. 6, 2004.

(Continued)

*Primary Examiner* — Brian E Pellegrino
(74) *Attorney, Agent, or Firm* — Haynes and Boone LLP (57) ABSTRACT

Devices and methods fabricating devices having nanostructures that allow adhesion or growth of one cell type, such as endothelial cells, more than another cell type, such as smooth muscle cells. In particular, stent covers may have nanostructures that allow adhesion or growth of one cell type more than another cell type. Nanostructures forming the devices may be optimized.

9 Claims, 6 Drawing Sheets

(56) References Cited

U.S. PATENT DOCUMENTS

| | | |
|---|---|---|
| 1,904,828 A | 4/1933 | Green |
| 1,913,035 A | 6/1933 | Loepsinger |
| 1,926,925 A | 9/1933 | Wescott |
| 2,060,593 A | 11/1936 | Schaurte et al. |
| 2,371,614 A | 3/1945 | Graves |
| 2,586,556 A | 2/1952 | Mullikin |
| 2,608,996 A | 9/1952 | Forman |
| 2,610,300 A | 9/1952 | Walton et al. |
| 2,647,017 A | 7/1953 | Coulliette |
| 2,793,036 A | 5/1957 | Hansburg |
| 2,911,504 A | 11/1959 | Cohn |
| 3,229,956 A | 1/1966 | White |
| 3,351,463 A | 11/1967 | Rozner et al. |
| 3,357,432 A | 12/1967 | Sparks |
| 3,400,906 A | 9/1968 | Stocklin |
| 3,408,890 A | 11/1968 | Bochman, Jr. |
| 3,435,823 A | 4/1969 | Edwards |
| 3,445,086 A | 5/1969 | Quinn |
| 3,454,286 A | 7/1969 | Anderson et al. |
| 3,546,996 A | 12/1970 | Grijalva et al. |
| 3,559,641 A | 2/1971 | Lay |
| 3,561,537 A | 2/1971 | Dix et al. |
| 3,613,732 A | 10/1971 | Willson et al. |
| 3,620,212 A | 11/1971 | Fannon, Jr. et al. |
| 3,659,625 A | 5/1972 | Coiner et al. |
| 3,668,131 A | 6/1972 | Banush et al. |
| 3,725,835 A | 4/1973 | Hopkins et al. |
| 3,789,838 A | 2/1974 | Fournier et al. |
| 3,849,756 A | 11/1974 | Hickling |
| 3,888,975 A | 6/1975 | Ramwell |
| 3,913,572 A | 10/1975 | Wheeler |
| 3,918,443 A | 11/1975 | Vennard et al. |
| 3,974,844 A | 8/1976 | Pimentel |
| 3,991,898 A | 11/1976 | Hanson et al. |
| 4,055,955 A | 11/1977 | Johnson |
| 4,063,831 A | 12/1977 | Meuret |
| 4,072,159 A | 2/1978 | Kurosawa |
| 4,096,993 A | 6/1978 | Behr |
| 4,145,764 A | 3/1979 | Kuzuki et al. |
| 4,151,064 A | 4/1979 | Kuehnle |
| 4,176,719 A | 12/1979 | Bray |
| 4,177,327 A | 12/1979 | Mathews |
| 4,243,963 A | 1/1981 | Jameel et al. |
| 4,265,684 A | 5/1981 | Boll |
| 4,279,190 A | 7/1981 | Hummel |
| 4,340,049 A | 7/1982 | Munsch |
| 4,434,855 A | 3/1984 | Given, Jr. et al. |
| 4,485,545 A | 12/1984 | Caverly |
| 4,501,058 A | 2/1985 | Schutzler |
| 4,524,343 A | 6/1985 | Morgan et al. |
| 4,549,717 A | 10/1985 | Dewaegheneire |
| 4,551,974 A | 11/1985 | Yaeger et al. |
| 4,553,393 A | 11/1985 | Ruoff |
| 4,553,602 A | 11/1985 | Pieczykolan |
| 4,558,715 A | 12/1985 | Walton et al. |
| 4,567,549 A | 1/1986 | Lemme |
| 4,585,209 A | 4/1986 | Aine et al. |
| 4,589,179 A | 5/1986 | Hulting, Jr. |
| 4,596,483 A | 6/1986 | Gabriel et al. |
| 4,619,284 A | 10/1986 | Delarue et al. |
| 4,654,191 A | 3/1987 | Krieg |
| 4,684,913 A | 8/1987 | Yaeger |
| 4,706,758 A | 11/1987 | Johnson |
| 4,753,465 A | 6/1988 | Dalby |
| 4,821,997 A | 4/1989 | Zdeblick |
| 4,823,607 A | 4/1989 | Howe et al. |
| 4,824,073 A | 4/1989 | Zdeblick |
| 4,848,388 A | 7/1989 | Waldbusser |
| 4,854,797 A | 8/1989 | Gourd |
| 4,864,824 A | 9/1989 | Gabriel et al. |
| 4,893,655 A | 1/1990 | Anderson |
| 4,896,728 A | 1/1990 | Wolff et al. |
| 4,915,773 A | 4/1990 | Kravetsky |
| 4,943,032 A | 7/1990 | Zdeblick |
| 5,044,947 A | 9/1991 | Sachdeva et al. |
| 5,060,888 A | 10/1991 | Vezain et al. |
| 5,061,137 A | 10/1991 | Gourd |
| 5,061,914 A | 10/1991 | Busch et al. |
| 5,069,419 A | 12/1991 | Jerman |
| 5,072,288 A | 12/1991 | MacDonald et al. |
| 5,102,276 A | 4/1992 | Gourd |
| 5,114,504 A | 5/1992 | AduJudom, II et al. |
| 5,116,252 A | 5/1992 | Hartman |
| 5,117,916 A | 6/1992 | Ohta et al. |
| 5,119,555 A | 6/1992 | Johnson |
| 5,129,753 A | 7/1992 | Wesley et al. |
| 5,131,843 A | 7/1992 | Hilgers et al. |
| 5,160,233 A | 11/1992 | McKinnis |
| 5,190,546 A | 3/1993 | Jervis |
| 5,192,147 A | 3/1993 | McCloskey |
| 5,211,371 A | 5/1993 | Coffee |
| 5,218,998 A | 6/1993 | Bakken et al. |
| 5,245,738 A | 9/1993 | Johnson |
| 5,309,717 A | 5/1994 | Minch |
| 5,312,152 A | 5/1994 | Woebkenberg, Jr. et al. |
| 5,312,247 A | 5/1994 | Sachdeva |
| 5,325,880 A | 7/1994 | Johnson et al. |
| 5,344,117 A | 9/1994 | Trah et al. |
| 5,364,046 A | 11/1994 | Dobbs et al. |
| 5,395,238 A | 3/1995 | Andreiko et al. |
| 5,447,432 A | 9/1995 | Andreiko et al. |
| 5,456,600 A | 10/1995 | Andreiko et al. |
| 5,474,448 A | 12/1995 | Andreiko et al. |
| 5,474,563 A | 12/1995 | Myler et al. |
| 5,494,113 A | 2/1996 | Polan |
| 5,502,982 A | 4/1996 | Venetucci |
| 5,543,349 A | 8/1996 | Kurtz et al. |
| 5,605,543 A | 2/1997 | Swanson |
| 5,619,177 A | 4/1997 | Johnson et al. |
| 5,622,225 A | 4/1997 | Sundholm |
| 5,640,217 A | 6/1997 | Hautcoeur et al. |
| 5,641,364 A | 6/1997 | Golberg et al. |
| 5,645,423 A | 7/1997 | Collins, Jr. |
| 5,658,515 A | 8/1997 | Lee et al. |
| 5,676,356 A | 10/1997 | Ekonen et al. |
| 5,683,245 A | 11/1997 | Sachdeva et al. |
| 5,695,504 A | 12/1997 | Gifford, III et al. |
| 5,714,690 A | 2/1998 | Burns et al. |
| 5,722,989 A | 3/1998 | Fitch et al. |
| 5,771,742 A | 6/1998 | Bokaie et al. |
| 5,772,378 A | 6/1998 | Keto-Tokoi |
| 5,772,864 A | 6/1998 | Moller et al. |
| 5,796,152 A | 8/1998 | Carr et al. |
| 5,819,749 A | 10/1998 | Lee et al. |
| 5,825,275 A | 10/1998 | Wuttig et al. |
| 5,837,394 A | 11/1998 | Schumm, Jr. |
| 5,840,199 A | 11/1998 | Warren |
| 5,850,837 A | 12/1998 | Shiroyama et al. |
| 5,867,302 A | 2/1999 | Fleming |
| 5,903,099 A | 5/1999 | Johnson et al. |
| 5,916,178 A | 6/1999 | Noone et al. |
| 5,924,492 A | 7/1999 | Kikuchi et al. |
| 5,930,651 A | 7/1999 | Terasawa |
| 5,960,812 A | 10/1999 | Johnson |
| 6,013,854 A | 1/2000 | Moriuchi |
| 6,042,374 A | 3/2000 | Farzin-Nia et al. |
| 6,042,553 A | 3/2000 | Solar et al. |
| 6,072,617 A | 6/2000 | Henck |
| 6,073,700 A | 6/2000 | Tsuji et al. |
| 6,075,239 A | 6/2000 | Aksyuk et al. |
| 6,080,160 A | 6/2000 | Chen |
| 6,084,849 A | 7/2000 | Durig et al. |
| 6,096,175 A | 8/2000 | Roth |
| 6,101,164 A | 8/2000 | Kado et al. |
| 6,107,004 A | 8/2000 | Donadio, III |
| 6,110,204 A | 8/2000 | Lazarov et al. |
| 6,123,153 A | 9/2000 | Finnegan |
| 6,124,523 A | 9/2000 | Banas et al. |
| 6,126,371 A | 10/2000 | McCloskey |
| 6,129,153 A | 10/2000 | Joung |
| 6,139,143 A | 10/2000 | Brune et al. |
| 6,169,269 B1 | 1/2001 | Maynard |
| 6,195,478 B1 | 2/2001 | Fouquet |
| 6,203,715 B1 | 3/2001 | Kim et al. |

(56) References Cited

U.S. PATENT DOCUMENTS

| | | |
|---|---|---|
| 6,224,626 B1 | 5/2001 | Steinke |
| 6,229,640 B1 | 5/2001 | Zhang |
| 6,247,493 B1 | 6/2001 | Henderson |
| 6,277,133 B1 | 8/2001 | Kanesaka |
| 6,284,067 B1 | 9/2001 | Schwartz et al. |
| 6,352,494 B2 | 3/2002 | McAlonan |
| 6,358,380 B1 | 3/2002 | Mann et al. |
| 6,379,383 B1 | 4/2002 | Palmaz et al. |
| 6,386,507 B2 | 5/2002 | Dhuler et al. |
| 6,406,605 B1 | 6/2002 | Moles |
| 6,407,478 B1 | 6/2002 | Wood et al. |
| 6,410,360 B1 | 6/2002 | Steenberge |
| 6,419,491 B1* | 7/2002 | Ricci .................. A61F 2/30771 433/173 |
| 6,447,478 B1 | 9/2002 | Maynard |
| 6,451,668 B1 | 9/2002 | Neumeier et al. |
| 6,454,913 B1 | 9/2002 | Rasmussen et al. |
| 6,470,108 B1 | 10/2002 | Johnson |
| 6,475,261 B1 | 11/2002 | Matsumoto et al. |
| 6,524,322 B1 | 2/2003 | Berreklouw |
| 6,533,905 B2 | 3/2003 | Johnson et al. |
| 6,537,310 B1 | 3/2003 | Palmaz et al. |
| 6,582,985 B2 | 6/2003 | Cabuz et al. |
| 6,592,724 B1 | 7/2003 | Rasmussen et al. |
| 6,596,102 B2 | 7/2003 | Homma |
| 6,605,111 B2 | 8/2003 | Bose et al. |
| 6,614,570 B2 | 9/2003 | Johnson et al. |
| 6,620,634 B2 | 9/2003 | Johnson et al. |
| 6,624,730 B2 | 9/2003 | Johnson et al. |
| 6,669,794 B1 | 12/2003 | Bellouard et al. |
| 6,669,795 B2 | 12/2003 | Johnson et al. |
| 6,672,502 B1 | 1/2004 | Paul et al. |
| 6,688,828 B1 | 2/2004 | Post |
| 6,709,379 B1* | 3/2004 | Brandau et al. ............. 623/1.39 |
| 6,729,599 B2 | 5/2004 | Johnson |
| 6,742,761 B2 | 6/2004 | Johnson et al. |
| 6,746,890 B2 | 6/2004 | Gupta et al. |
| 6,771,445 B1 | 8/2004 | Hamann et al. |
| 6,790,298 B2 | 9/2004 | Johnson et al. |
| 6,805,898 B1* | 10/2004 | Wu et al. ..................... 623/1.46 |
| 6,811,910 B2 | 11/2004 | Tsai et al. |
| 6,820,676 B2 | 11/2004 | Palmaz et al. |
| 6,821,638 B2* | 11/2004 | Obeshaw .................. B32B 3/30 428/596 |
| 6,840,329 B2 | 1/2005 | Kikuchi et al. |
| 6,843,465 B1 | 1/2005 | Scott |
| 6,849,085 B2 | 2/2005 | Marton |
| 6,852,132 B1 | 2/2005 | Houser et al. |
| 6,908,275 B2 | 6/2005 | Nelson et al. |
| 6,918,545 B2 | 7/2005 | Franson et al. |
| 6,920,966 B2 | 7/2005 | Buchele et al. |
| 6,923,829 B2 | 8/2005 | Boyle et al. |
| 6,955,187 B1 | 10/2005 | Johnson |
| 7,022,173 B2 | 4/2006 | Cummings et al. |
| 7,040,323 B1 | 5/2006 | Menchaca et al. |
| 7,044,596 B2 | 5/2006 | Park |
| 7,073,504 B2 | 7/2006 | Callister et al. |
| 7,084,726 B2 | 8/2006 | Gupta et al. |
| 7,201,367 B2 | 4/2007 | Wietharn |
| 7,229,500 B2 | 6/2007 | Haushalter et al. |
| 7,235,092 B2 | 6/2007 | Banas et al. |
| 7,235,096 B1 | 6/2007 | Van Tassel et al. |
| 7,235,098 B2 | 6/2007 | Palmaz |
| 7,422,403 B1 | 9/2008 | Johnson et al. |
| 7,441,888 B1 | 10/2008 | Johnson |
| 7,524,914 B2* | 4/2009 | Mather et al. .................. 528/28 |
| 7,540,899 B1 | 6/2009 | Johnson |
| 7,544,257 B2 | 6/2009 | Johnson et al. |
| 7,586,828 B1 | 9/2009 | Xiaogdang |
| 7,632,361 B2 | 12/2009 | Johnson et al. |
| 7,736,687 B2 | 6/2010 | Sims et al. |
| 7,763,342 B2 | 7/2010 | Johnson |
| 7,793,911 B2 | 9/2010 | Fontana et al. |
| 7,842,143 B2 | 11/2010 | Johnson et al. |
| 2001/0023010 A1 | 9/2001 | Yamada et al. |
| 2002/0018325 A1 | 2/2002 | Nakatani et al. |
| 2002/0062154 A1 | 5/2002 | Ayers |
| 2002/0106614 A1 | 8/2002 | Prince et al. |
| 2002/0192617 A1 | 12/2002 | Phan et al. |
| 2003/0002994 A1 | 1/2003 | Johnson et al. |
| 2003/0054578 A1* | 3/2003 | Behfar .................. B81C 99/008 438/761 |
| 2003/0078465 A1 | 4/2003 | Pai et al. |
| 2003/0170130 A1 | 9/2003 | Johnson |
| 2004/0083006 A1 | 4/2004 | Ellingsen |
| 2004/0200551 A1 | 10/2004 | Brhel et al. |
| 2004/0221614 A1 | 11/2004 | Holemans et al. |
| 2004/0243219 A1 | 12/2004 | Fischer et al. |
| 2004/0249399 A1 | 12/2004 | Cinquin et al. |
| 2005/0112397 A1* | 5/2005 | Rolfe ...................... A61L 27/56 623/23.74 |
| 2005/0113933 A1 | 5/2005 | Carter et al. |
| 2006/0118210 A1 | 6/2006 | Johnson |
| 2006/0204738 A1 | 9/2006 | Dubrow et al. |
| 2006/0213522 A1 | 9/2006 | Menchaca et al. |
| 2006/0240953 A1 | 10/2006 | Shahinpoor |
| 2007/0134296 A1* | 6/2007 | Burgermeister ........ A61L 31/14 424/426 |
| 2007/0173787 A1* | 7/2007 | Huang et al. ............. 604/891.1 |
| 2007/0207321 A1 | 9/2007 | Abe et al. |
| 2007/0246233 A1 | 10/2007 | Johnson |
| 2008/0075557 A1 | 3/2008 | Johnson et al. |
| 2008/0161936 A1 | 7/2008 | Feller et al. |
| 2008/0213062 A1 | 9/2008 | Johnson |
| 2009/0029077 A1* | 1/2009 | Atanasoska et al. ......... 427/300 |
| 2009/0035859 A1 | 2/2009 | Johnson |
| 2009/0166318 A1* | 7/2009 | Seitz .................. H01L 21/0332 216/13 |
| 2009/0183986 A1 | 7/2009 | Johnson et al. |
| 2009/0187243 A1 | 7/2009 | Johnson |
| 2010/0006304 A1 | 1/2010 | Johnson et al. |
| 2010/0025050 A2 | 2/2010 | Johnson et al. |
| 2010/0129766 A1 | 5/2010 | Hilgers |
| 2010/0190127 A1 | 7/2010 | Ghantiwala et al. |
| 2011/0083767 A1 | 4/2011 | Johnson |
| 2011/0253525 A1 | 10/2011 | Johnson et al. |

FOREIGN PATENT DOCUMENTS

| | | |
|---|---|---|
| EP | 0836839 A2 | 4/1998 |
| EP | 1122526 | 8/2001 |
| EP | 1238600 | 9/2002 |
| EP | 1779817 A1 | 5/2007 |
| EP | 1967218 A2 | 9/2008 |
| GB | 2187951 | 9/1987 |
| JP | 48071713 A | 9/1973 |
| JP | 57161031 | 10/1982 |
| JP | 58088200 A | 5/1983 |
| JP | 59179771 | 10/1984 |
| JP | 07090624 | 4/1995 |
| JP | 10173306 | 6/1998 |
| JP | 2000185999 A | 7/2000 |
| SU | 1434314 | 10/1988 |
| WO | WO98/42277 A1 | 10/1998 |
| WO | WO98/53362 | 11/1998 |
| WO | WO99/16387 A1 | 4/1999 |
| WO | WO99/62432 | 12/1999 |
| WO | WO00/04204 | 1/2000 |
| WO | WO01/35865 | 5/2001 |
| WO | WO03/52150 | 6/2003 |
| WO | WO2005/084582 | 9/2005 |
| WO | WO2005/108635 | 11/2005 |
| WO | WO2006/019943 | 2/2006 |
| WO | WO2006/044904 | 4/2006 |
| WO | WO2007/078304 | 7/2007 |
| WO | WO2008/054408 | 5/2008 |

OTHER PUBLICATIONS

Johnson et al.; U.S. Appl. No. 11/948,852 entitled "Method of alloying reactive elemental components," filed Nov. 30, 2007.

(56) References Cited

OTHER PUBLICATIONS

Antonov et al.; New advances and developments in the Stepnakov method for the growth of shaped crystals; Crystallography Reports; vol. 47; Suppl. 1; 2002; pp. S43-S52.

Brice et al.; Crystal Growth; Ullmann's Encyclopedia of Industrial Chemistry; 2007; Wiley-VCH Verlag GmBH; pp. 1, 29-42, 50.

Buchaillot et al., "Thin film of titanium/nickel shape memory alloy for multi-degree of freedom microactuators", Seisan Kenkyu, vol. 51, No. 8, 1999, pp. 22-23.

Creuziger et al.; Initial transformation around a notch tip in CuAlNi: experiment and modeling; Acta Materialia; vol. 56; pp. 518-526; 2008.

Christian et al.; The application of shape memory actuators in anthropomorphic upper limb prostheses; Artif. Organs; vol. 27; No. 5; pp. 473-477; 2003.

Dario et al.; Shape memory alloy microactuators for minimal invasive surgery; Proceedings of SMST-94 Conference; pp. 427-433; Pacific Grove CA; 1994.

ElastametTM brochure from New Discovery Metals; 2007.

ElastametTM website screen capture, accessed Jul. 23, 2008.

Fu et al.; The growth characteristics with a shape memory effect; J. Phys.: Condens. Matter; vol. 4; 1992; pp. 8303-8310.

Gill et al.; Three-Dimensional Thin-Film Shape Memory Alloy Microactuator With Two-Way Effect; Journal of Microelectromechanical Sys.; vol. 11; No. 1; pp. 68-77; Feb. 2002.

http://www.algor.com/news_pub/tech_reports/2005/rubber&foam/default.asp.

Johnson et al., "Application of shape memory alloys: advantages, disadvantages, and limitations," Micromachining and Microfabrication Process Technology VII, 22-4, Oct. 2001, San Francisco, CA, USA, vol. 4557, pp. 341-351.

Johnson, A. D.; Vacuum-deposited TiNi shape memory film: Characterization and applications in microdevices; J. Micromech. Microeng.; vol. 1; pp. 34-41; 1991.

Krulevitch et al.; Thin film shape memory alloy microactuators; J. Micromech. Microeng.; vol. 5; No. 4; 26 pgs.; 1996.

Martynov, V., "TiNi thin films for microactuators and microdevices: sputter deposition and processing techniques", Thermec' 2003, Internat'l Conf. on Processing and Manufacturing of Advanced Materials, Jul. 7-11, 2003, Leganes, Madrid, Spain, Materials Science Forum, Jul. 7, 2003 vol. 426-432; pp. 3475-3480.

Morgan; Medical shape memory alloy applications—the market and its products; Materials Science and engineering A 378; 2004; pp. 16-23.

Pauling, Linus, College Chemistry, second edition, W.H. Freeman and Company, San Francisco, 1955, pp. 81-91.

Qingfu et al.; Stabilisation of martensite during training of Cu—Al—Ni single crystals; Journal de Physique IV; Colloqu C2; Supplement to the Journa de Physique III; vol. 5; Feb. 1995; pp. 181-186.

Recarte et al.; Influence of Al and Ni concentration on the martensitic transformation in Cu—Al—Ni shape-memory alloys; Metallurgical and MaterialsTransactions A; vol. 33A; Aug. 2002; pp. 2581-2591.

Schetky, L.M.; Shape-memory alloys; Scientific American, pp. 74-82; 1979.

Sittner et al.; Stress induced martensitic transformations in tension/torsion of CuAlNi single crystal tube; Scripta Materialia; vol. 48; 2003; pp. 1153-1159.

Sutuo et al.; Development of medical guide wire of Cu—Al—Mn-base superelastic alloy with functionally graded characteristics; Mater Res Part B: Appl Biomater; vol. 69B; 2004; pp. 64-69.

Takabayashi et al., "Reversible shape memory alloy film fabricated by RF sputtering", Materials and Manufacturing Processes, vol. 13, No. 2, 1998, pp. 275-286.

Viahhi et al.; "Robototechnic Constructions Based on Cu—Al—Ni Single Crystal Actuators;" Proceedings of Second International Conference on Shape Memory and Superelastic Technologies; 1997; United States.

Wang et al.; Temperature memory effect in CuAlNi single crystalline and CUZnAl polycrystalline shape memory alloys; Thermochimica Acta; vol. 448; 2006; pp. 69-72.

Yahia et al.; Bioperformance of shape memory alloy single crystals; Bio-Medical Materials and Engineering; vol. 16; 2006; pp. 101-118.

Zhang et al.; Nanoscale pseudoelasticity of single-crystal Cu—Al—Ni shape-memory alloy induced by cyclic nanoindentation; J Mater Sci; vol. 41; 2006; pp. 5021-5024.

Zhang et al.; The variant selection criteria in single-crystal CuAlNi shape memory alloys; Smart Mater. Struct.; vol. 9; 2000; pp. 571-581.

Zhdanov et al.; Thermal stresses in tubes, produced from a melt by the Stepanov method, during their cooling; Journal of Engineering Physics and Thermophysics; vol. 68; No. 1; 1995; pp. 80-89.

Balasundaram et al; Using hydroxyapatite nanoparticles and decreased crystallinity to promote osteoblast adhesion similar to functionalizing with RGD; Biomaterials; vol. 27; 2006; pp. 2798-2805.

Barbucci et al.; Micro and nano-structured surfaces; Journal of Materials Science: Materials in Medicine; vol. 14; 2003; pp. 721-725.

Barbucci et al.; Micropatterned surfaces for the control of endothelial cell behaviour; Bimolecular Engineering; vol. 19; 2002; pp. 161-170.

Brock et al.; Geometric determinants of directional cell motility revealed using microcontact printing; Langmuir; vol. 19; 2003; pp. 1611-1617.

Castner et al.; Biomedical surface science: Foundations to frontiers; Surface Science; vol. 500; 2002; pp. 28-60.

Chen et al.; Geometric control of cell life and death; Science; vol. 276; May 30, 1997; pp. 1425-1428.

Faghihi et al.; The significance of crystallographic texture of titanium alloy substrates on pre-osteoblast responses; Biomaterials; vol. 27; 2006; pp. 3532-3539.

Gall et al.; Tensile deformation of NiTi wires; J Biomed Mater Res; vol. 75A; 2005; pp. 810-823.

Geissler et al.; Patterning: Principles and some new developments; Advanced Materials; vol. 16; No. 15; Aug. 4, 2004; pp. 1249-1269.

Hassel; Surface treatment of NiTi for medical applications; Min. Invas. Ther. & Allied Tech.; vol. 13; No. 4; 2004; pp. 240-247.

Ingber; Tensegrity II. How structural networks influence cellular information processing networks; Journal of Cell Science; vol. 116; 2003; pp. 1397-1408.

Jiang et al.; Directing cell migration with asymmetric micropatterns; PNAS; vol. 102; No. 4; Jan. 25, 2005; pp. 975-978.

Lam et al.; The attachment, proliferation, and wound healing of endothelial and smooth muscle cells on nitinol thin film in vitro; Proc. of the 26th Ann. Intl. Conf. of the IEEE EMBS; San Franciso, CA, USA; Sep. 1-5, 2004; pp. 5044-5046.

Lu et al.; Endothelial cell adhesion on highly controllable compared to random nonostructured titanium surface features; Mater. Res. Soc. Symp. Proc.; vol. 951; 2007.

Magnani et al.; Cell behaviour on chemically microstructured surfaces; Materials Science and Engineering; vol. C 23; 2003; pp. 315-328.

Mai et al.; A microfabricated platform probing cytoskeleton dynamics using mulidirectional topographical cues; Biomed Microdevices; vol. 9; 2007; pp. 523-531.

Miller et al.; PLGA nanometer surface features manipulate fibronectin interactions for improved vascular cell adhesion; Journal of Biomedical Materials Research; Part A; 81A; Issue 3; pp. 678-684; Dec. 22, 2006.

Monsees et al.; Effects of different titanium alloys and nonosize surface patterning on adhesion, differentiation, and orientation of osteoblast-like cells; Cells Tissues Organs, Karger, Basel, CH; vol. 180; No. 2; pp. 81-95; Jan. 1, 2005.

Morra; Biochemical modification of titanium surfaces: peptides and ECM proteins; European Cells and Materials; vol. 12; 2006; pp. 1-15.

Nelson et al.; Degradation of micropatterned surfaces by cell-dependent and -independent processes; Langmuir; Jul. 1, 2002; pp. A-G.

Pattison et al.; Three-dimensional, nano-structured PLGA scaffolds for bladder tissue replacement applications; Biomaterials; vol. 26; 2005; pp. 2491-2500.

(56) References Cited

OTHER PUBLICATIONS

Pelton et al.; A guide to shape memory and superelasticity in nitinol medical devices; Min. Invas. Ther. & Allied Tech.; vol. 13; No. 4; 2004; pp. 218-221.
Price et al.; Nanometer surface roughness increases select osteoblast adhesion on carbon nanofiber compacts; J Biomed Mater Res; vol. 70A; 2004; pp. 129-138.
Robertson et al.; Crystallographic texture for tube and plate of the superelastic/shape-memory alloy nitinol used for endovascular stents; J Biomed Mater Res; vol. 72A; 2005; pp. 190-199.
Sagvolden et al.; Cell adhesion force microscopy; Proc. Natl. Acad. Sci. USA; vol. 96; Jan. 1999; pp. 471-476.
Sato et al.; Nanobiotechnology: implications for the future of nanotechnology in orthopedic applications; Expert Rev. Medical Devices; vol. 1; No. 1; 2004; pp. 105-114.
Shaikh-Mohammed et al.; Cell adhesion testing using novel testbeds containing micropatterns of complex nanoengineered multilayer films; Proc. of the 26th Ann. Intl. Conf. of the IEEE EMBS; San Francisco, CA, USA; Sep. 1-5, 2004; pp. 2671-2674.
Stevens et al.; Exploring and engineering the cell surface interface; Science; vol. 310; Nov. 18, 2005; pp. 1135-1138.
Stoeckel et al.; Self-expanding nitinol stents: material and design considerations; Eur. Radiol.; vol. 14; 2004; pp. 292-301.
Thapa et al.; Polymers with nano-dimensional surface features enhance bladder smooth muscle cell adhesion; J. Biomed Mater Res; vol. 67A; 2003; pp. 1374-1383.
Thierry et al.; Effect of surface treatment and sterilization processes on the corrosion behaviour of NiTi shape memory alloy; J. Biomed Mater Res; vol. 51; 2000; pp. 685-693.
Tourovskaia et al.; Micropatterns of chemisorbed cell adhesion-repellent films using oxygen plasma etching and elastomeric masks; Langmuir; vol. 19; 2003; pp. 4754-4764.
Trépanier et al.; Preliminary investigation of the effects of surface treatments on biological response to shape memory NiTi stents; J. Biomed Mater Res (Appl Biomater); vol. 48; 1999; pp. 165-171.
Vastag; Stents stumble—Enthursiasm wanes for drug-coated artery tubes; Science; vol. 171; pp. 394-395; Jun. 23, 2007.
Wang et al.; Control of cytoskeletal mechanics by extracellular matrix, cell shape, and mechanical tension; Biophysical Journal; vol. 66; Jun. 1994; pp. 2181-2189.
Webster et al.; Increased osteoblast adhesion on titanium-coated hydroxylapatite that forms CaTiO3; J Biomed Mater Res; vol. 67A; 2003; pp. 975-980.
Webster et al.; Nanoceramic surface roughness enhances osteoblast and osteoclast functions for improved orthopaedic/dental implant efficacy; Scripta mater.; vol. 44; 2001; pp. 1639-1642.
Webster; Nanotechnology for healing damaged vascular tissue; posted May 4, 2007; www.scitizen.com/screens/blogPage/viewBlog.
Webster; Nonotechnology: Better materials for all implants; Mat. Science Forum; vols. 539-543; 2007; pp. 511-516.
Wirth et al.; Nitinol surface roughness modulates in vitro cell response: a comparison between fibroblasts and osteoblasts; Mat. Science and Eng.; vol. C 25; 2005; pp. 51-60.
Zhang et al.; Biological surface engineering: a simple system for cell pattern formation; Biomaterials; vol. 20; 1999; pp. 1213-1220.
Johnson et al.; U.S. Appl. No. 13/215,438 entitled "Shape setting a shape memory alloy dental arch," filed Aug. 23, 2011.
Johnson, Alfred David; U.S. Appl. No. 13/601,749 entitled "Fire Sprinkler Valve Actuator," filed Aug. 31, 2012.

* cited by examiner

METHOD AND DEVICES FOR PREVENTING RESTENOSIS IN CARDIOVASCULAR STENTS

CROSS REFERENCE TO RELATED APPLICATIONS

This application is a divisional of U.S. patent application Ser. No. 12/182,119, filed on Jul. 29, 2008, entitled "METHOD AND DEVICES FOR PREVENTING RESTENOSIS IN CARDIOVASCULAR STENTS", which claims priority to U.S. Provisional Application No. 60/952,818 filed on Jul. 30, 2007, entitled, "METHOD AND DEVICES FOR PREVENTING RESTENOSIS IN CARDIOVASCULAR STENTS."

INCORPORATION BY REFERENCE

All publications and patent applications mentioned in this specification are herein incorporated by reference in their entirety, as if each individual publication or patent application was specifically and individually indicated to be incorporated by reference.

BACKGROUND OF THE INVENTION

Stents have become the treatment of choice for a variety of blood vessel diseases in humans and are in common use worldwide. From the beginning of their use, it is known that an unacceptable percentage of cardiac stents become blocked after installation. This restenosis is a serious health problem: a patient may be more seriously impaired after treatment than before. Restenosis occurs when smooth muscle cells in the blood aggregate into clumps and cause the stent to become occluded. Drug-eluting coatings have been used to prevent clumping. Based on current data, it now appears that these coatings are not a satisfactory solution. For example, coated stents have been shown to cause blood clots several years after installation (Brian Vastag, "Stents Stumble," Science News, Jun. 23, 2007 Vol. 171, pp 394-395). A patient receiving a coated stent must use blood thinners to prevent formation of blood clots that may dislodge from the region of the stent and cause stroke or heart attack. If the blood thinning treatment is interrupted, the probability of stroke is greatly increased. Thus, coated stents have therefore proved not to be a viable solution to the problem of stent restenosis.

It has recently been proposed that the restenosis of a stent is largely determined by whether the first layer of cells to grow on the surface of a stent are endothelial cells or smooth muscle cells (Julio Palmaz, Lecture at SMST conference 2003, Asilomar Calif. Comments not included in Proceedings of the conference). Described herein are stent covers which selectively enable endothelial cells to grow on their surface in comparison to smooth muscle cells, as well as methods of manufacturing and using them.

Other methods of preventing restenosis have been developed. For example, Palmaz describes a method using chemical affinities (resulting from charges on the surface of the stent) to regulate the growth of endothelial cells versus smooth muscle cells. U.S. Pat. No. 6,820,676 to Palmaz et al. teaches the use of surface relief patterns corresponding to crystal boundaries in metal to the enhance growth of cells. However, these patterns are irregular in size and shape and so are not ideally selective for a specific protein. In WO07078304A2, Dubrow et al. suggest using fibers (e.g., nanofibers or nanowires) to form a substrate for use in various medical devices.

Stents using shape memory alloys (e.g., Nitinol) to form thin-film stent covers are currently being developed. For example, US 2008/0161936 to Feller et al. describes a stent including a thin-film of shape memory alloy having different porosities in the deployed and undeployed configurations. A stent cover is typically placed over a stent to provide protection against debris that may be dislodged during installation of the stent. Described herein are stents or stent covers including a thin film coating or surface that preferably selects endothelial cells (e.g., from the blood stream) to grow on the inside surface of a thin-film stent or stent cover compared to other cell types (e.g., smooth muscle cells). This may be accomplished by forming nanostructures on the inside of the stent or stent cover. These nanostructures may be formed of one or more layers, and may correspond to recurring patterns on endothelial cell membrane proteins. Endothelial cells that come in contact with the surface nanostructures may selectively adhere to them. For example, endothelial cells (as opposed to smooth muscle cells) may 'recognize' the surface structure by pattern matching (or pattern recognition) and adhere. This pattern recognition step is a key element in many molecular biology processes. The devices and methods described herein take advantage of this native molecular biological process (e.g., cell-surface interactions) to influence the adherence of one type of cell (e.g. endothelial cells) in preference to other types (e.g. smooth muscle cells). Thus, surface nanostructures may be used to selectively enhance adhesion of endothelial cells over smooth muscle cells.

SUMMARY OF THE INVENTION

General methods of forming thin-film, nano-scale layered substrates appropriate for controlled cell growth are described herein. In addition, we describe particular applications of such nano-layered controlled growth substrates. In particular, described herein are implantable medical devices having nanostructures that allow adhesion and/or growth of one cell type, such as endothelial cells, more than another cell type, such as smooth muscle cells. For example, stents and stent covers having such nanostructures are described. Methods for fabricating these devices are also described.

For example, described herein are methods of controlling the growth of cells, including differential or preferential growth of cells, including the steps of patterning a substrate to have an organized nanostructure for cell growth, and placing cells on the patterned substrate. Cells may be regulated or controlled in any number of ways by the nanostructured surfaces described herein, including, as mentioned, differential growth (e.g., of various different cell types), cell guidance (e.g., axon guidance, cell migration, etc.), apoptosis, inhibition of cell growth, and the like.

A substrate may be patterned by: (a) layering a first nanostructural material at least partially over a substrate; (b) layering a second nanostructural material at least partially over the layer from step a; (c) repeating steps a and b to form a plurality of alternating layers of the first nanostructural material and the second nanostructural material; (d) forming a patterned layer on the outer surface of the plurality of alternating layers; and (e) etching the nonstructural material to form a nanostructured surface. In some variations, the step of layering the second nanostructural material comprises depositing a shape memory alloy at least partially over the first nanostructural material layer. The shape memory alloy may also be crystallized.

In general, these substrates are different from other cell culture substrates because they are formed using lithographic procedures to have sides or walls that are alternating layers or striated layers, of nanostructural materials (e.g., metals, alloys, polymers, etc.) that can be repeated patterns may layers thick. For example, one well or islet may have walls comprising five, ten, fifteen, twenty, twenty-five, fifty or even a hundred or more alternating layers of nanostructural materials. Each layer (or sub-layer) may be extremely thin (e.g., on the order of a few nm of thickness), and differ layers may have different thicknesses. The geometry may be important. For example, not only the thickness of each layer (or sub-layer), but the overall shape of the well or islet formed, as described in further detail below, may affect the growth or development of the cells contacting them.

For example, a method of forming a stent cover having a nanostructure includes the steps of forming a protective patterned layer on an outer surface of a sacrificial mandrel, layering a first nanostructural material at least partially over the protective patterned layer, depositing a shape memory alloy at least partially over the nanostructural material layer, crystallizing the shape memory alloy, removing the sacrificial mandrel, and etching the nonstructural material to form a nanostructured surface surrounded by a shape memory alloy thin film.

Any appropriate shape memory alloy may be used, including a nickel-titanium alloy (e.g., Nitinol), and the method may also include the step of fenestrating the shape memory alloy.

The sacrificial mandrel may be formed of an etchable metal, such as copper, that may be removed prior to etching the nanostructured layer. A protective patterned layer may be formed on the mandrel in order to pattern the nanostructural layer by acting as a resist layer to protect it (or a portion of it) during processing to form the nanostructural layer, particularly when the processing includes lithographic processing to form the nanostructural layer. The protective patterned layer may itself be formed on the mandrel photolithographically. For example, the protective patterned layer may be formed by coating a chromium layer on the sacrificial mandrel, applying a photoresistive layer, and then exposing it to a negative or positive of the desired protective pattern. For example, the protective patterned layer may be a checkerboard pattern to form islets of nanostructural material. In some variations, a pattern of wells may be formed.

Any appropriate material may be used as the nanostructural material. For example, the nanostructural material may include metals (including alloys), ceramics, polymers (including biopolymers), peptides (including polypeptides), nucleotides, composite materials, or the like. The nanostructural material may be a core matrix that is doped with additional materials. In some variations, the nanostructural material may be selected from the group consisting of: Ti, TiNi, Au, Ni, Al, Fe, Pt, Hf. Other materials having specific properties may be used, including those taught by Haushalter (U.S. Pat. No. 7,229,500). In some variations, the nanostructured layer includes a plurality of layers (including sub-layers). For example, a second nanostructural material may be at least partially applied over the protective patterned layer. The first nanostructural material may be applied to a thickness of between about 10 nm and about 500 nm. Similarly the second nanostructural material may be applied to a thickness of between about 10 nm and about 500 nm.

Also described herein are stent covers including nanostructures to which endothelial cells adhere preferentially compared to smooth muscle cells. A stent cover may include a thin-film of a shape memory material, the thin film at least partially surrounding a nanostructural layer, wherein the nanostructural layer comprises a layered nanoscale pattern having a shape and thickness that is selected so that endothelial cells preferentially adhere to the nanostructural layer as compared to smooth muscle cells.

As mentioned above, the shape memory material may be a nickel-titanium alloy (e.g., Nitinol). The shape memory material may further comprise fenestrations.

In some variations, the nanostructural layer comprises one or more pairs of sub-layers wherein each sub-layer is between about 10 nm and about 500 nm thick. The nanostructural layer may be at least partially made of a metal selected from the group consisting of: Ti, TiNi, Au, Ni, Al, Fe, Pt, Hf, and may have a thickness of between about 10 nm and about 500 nm. In some variations, the nanostructural layer comprises one or more sub-layers having a thickness of between about 10 nm and about 500 nm. Other materials having specific properties may be used, including those taught by Haushalter (U.S. Pat. No. 7,229,500).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Substrates, devices incorporating substrates, methods of forming substrates, and methods of forming devices including the substrates are described herein. In general, these substrates may be useful for tissue engineering. Surfaces such as those described herein that include structures having well-controlled shapes and sizes may provide means for controlling the behavior of individual cells and collections of cells (including tissues). Cells, and even tissues, may be controlled by controlling the arrangement of proteins.

Substrates including the patterned surfaces described herein (including those patterned using shape-memory materials) may provide surfaces on which controlled cell growth is enabled. These surfaces may be configured to select for cell type (e.g., enhancing the growth of certain cells compared to other cells). The structure of the surface may be the primary factor in regulating the cell behavior, rather than the chemical or material properties of the surface, as is commonly believed. The structure of the surface may also help manipulate the proteins on the surface of the cells and/or in the intracellular compartments of the cell.

The surface structures described herein are controlled over the dimension of the nanometer-to-micron scale. This scale (including the scale of the thickness of the layers) may be selected and controlled in a range of tens of nanometers to hundreds of nanometers, which is comparable to the size of most proteins. The scale of the micromachined structures (e.g., microns to tens of microns) is commensurate with the size of most cells. Thus, the methods described herein may allow the selection of proteins, which may be specific to certain types of cells, and of cell size and shape, which may also be specific to certain cell types. Taken together, these two selection methods may be much stronger than selection by either method alone. Unlike existing methods, which rely primarily on abrasion and have little or no control of the shape/size/pattern of the structures formed, these methods may create ordered and predictable patterns of surface structures having a predetermined shape and size. Typically, the layers forming the surfaces described herein are controlled to one percent or better.

The methods described herein may be used to create surfaces having organized arrangements of shapes. The shapes may be chosen based on the effect that the shape will have on cell behavior. For example, an elongated shape may encourage cell division (i.e., mitosis). A round shape may cause cells to undergo apoptosis (i.e., cell death). Other shapes may have different effects, such as encouraging migration or secretion. The thickness or shapes on the substrates described herein may also modify the expression of proteins on the surface of cells. For example, ledges that are of the same thickness dimension as a particular protein may enable formation of protein structures that do not occur in nature. A protein may bind to the surface in such a way that it is elongated rather than folded. If many proteins lie adjacent to each other in a stretched-out configuration, they may resemble (and may form) a novel crystal structure.

As mentioned, these substrates may be useful for growing tissues and organs. The location and spatial arrangement of individual cells in a multi-cell pattern may provide the scaffolding for development of specialized tissues.

FIGS. 1A-2D illustrate exemplary substrates, including patterns. These nano layered substrates may provide nanometer scale structures for use in cell growth experiments, for clinical cell growth, and for virtually any cell culture purpose. Furthermore, such surfaces may be included as part of a medical device (e.g., implant) or other medical interface, as described in greater detail below.

Figure 1A:
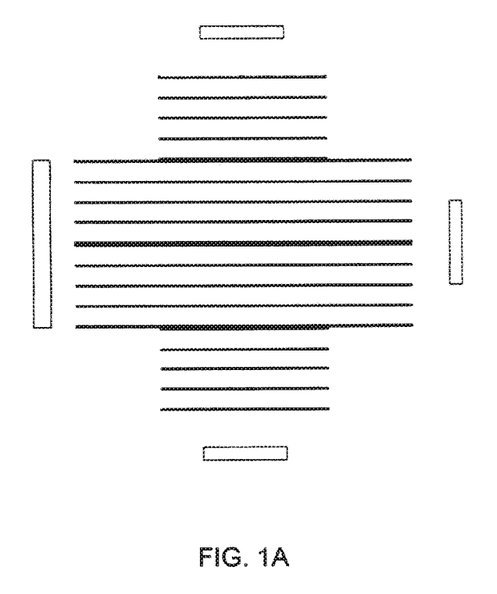
FIG. 1A shows a layout of a patterned wafer and FIGS. 1B and 1C illustrates examples of types of patterns for cell growth.

For example, FIG. 1A shows an exemplary pattern that may be formed on a silicon wafer or slide. In this example a thin film consisting of alternating layers of two materials (e.g., TiNi and Ti) are formed on a silicon die (slide). In this example, each layer may be vacuum sputter deposited to a thickness of between 10 and 250 nm. The thickness may be tightly controlled (e.g., a thickness of 10 nm for that layer may be approximately uniform at 10 nm), or it may be allowed to increase (e.g., ramp increase) across the layer. The actual thickness applied to the layer may be selected from the range (e.g., 10 to 250 nm) so that the final thickness is precisely known. Further, the number of layers formed of each material (e.g., TiNi, Ti, etc.) may be controlled. Typically multiple layers (e.g., 5 layers of each material, 10 layers of each material, 20 layers of each material, 30 layers of each material, etc.) may be chosen. The number of layers and the thickness of the layers may help form the complete thickness of the wells. As described in greater detail below, the side surfaces formed by these alternating layers (which may provide a striated or stratified side surface) may further create an ordered surface for cell or tissue growth. The different layers may be alternated in any desired pattern.

Figure 1B:
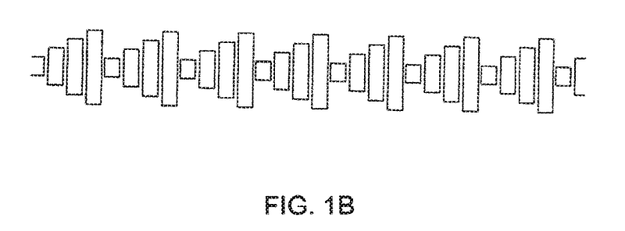
Figure 1C:
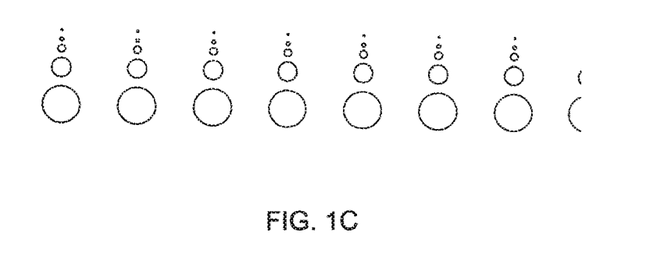

After deposition, wells may be created in the thin film by photolithographic techniques, including chemical etching. Wells may be between 1 and 10 microns in extent. The wells may have varying shapes and sizes to provide a variety of attachment conditions for cell development. FIG. 1A illustrates one example of a layout of a pattern on a wafer as viewed from the "macro" (naked eye) scale. Each horizontal line in this example indicates a row of one type of pattern. FIGS. 1B and 1C show different patterns that may be used. The images shown in FIGS. 1B and 1C are enlarged to show the shapes.

For example, the wafer shown in FIG. 1A may be divided up into 20 mm×20 mm slides. Each slide has approximately 50 rows of approximately 20 wells. In FIG. 1B, the rows (which may be included in the slide) have rectangular openings, and in FIG. 1C the rows five circular openings. The scale of these openings is between about 10 and about 400 microns in diameter. For example, the circles in FIG. 1C range in diameter from 10 to 200 microns (e.g., 10, 20, 40, 100, and 200 microns).

Figure 2A:
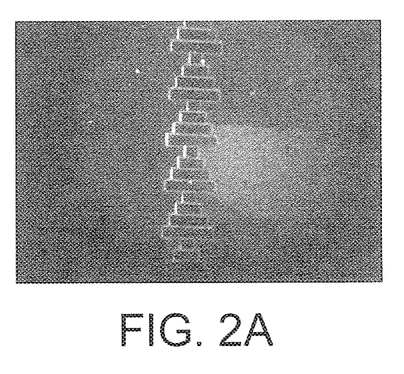
FIGS. 2A-2D show various etched patterns of Ti—Ni—Ti multi-layers on a substrate.
Figure 2B:
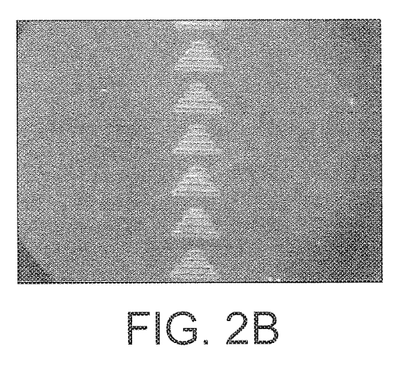
Figure 2C:
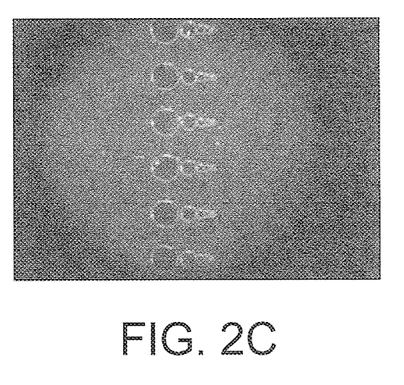
Figure 2D:
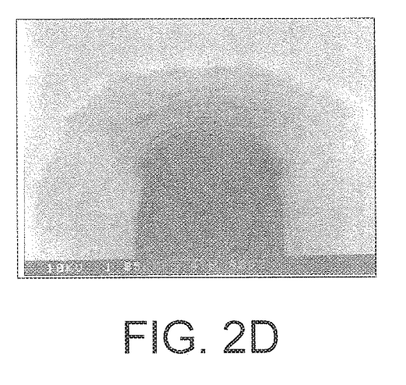

FIG. 2A-2D shows images of patterns etched in TiNi—Ti multi-layers on a silicon wafer, as briefly described above. For example, FIG. 2A shows a row of repeated rectangular openings. In one example, four groups of rectangular openings may be patterned. For example, the groups may be 10 microns wide by 100, 200, 300, and 400 microns long, 20 microns wide by 100, 200, 300, and 400 microns long, 40 microns wide by 100, 200, 300, and 400 microns long, and 80 microns wide by 100, 200, 300, and 400 microns long. The nanolayered substrates shown in FIGS. 2A-2C illustrate patterning of twenty alternating layers of Ti and TiNi deposited on a silicon or silicone oxide wafer surface to form a thin film that is 2 microns thick. The patterns of circles or rectangles can then be etched through the film. FIG. 2D shows an SEM image of a portion of an etched shape. The "walls" forming the shape are formed of the multiple layers of material, in this example, alternating layers of TiNi and Ti. The walls may be more or less 'steep' by controlling the etching or removal of the materials, and/or masking or protecting etched layers.

This general technique for forming a surface by patterning a substrate may be applied to substrates having non-flat (e.g. curved, bent, cylindrical, etc.) surfaces. For example, a medical implant, such as a catheter, stent, or the like, may include a nanolayered surface that is patterned appropriately to encourage and/or discourage cell growth or other cell behaviors.

Described below are stent covers and methods of forming stent covers having a preferentially patterned surface. For example, a method for determining a pattern that preferentially favors endothelial cell adhesion over smooth muscle cell adhesion is described. Although these methods are described with particular reference to stent covers, they may also be applied to the surface (particularly the "inner" or luminal surface) of a stent itself, or other structures, including other medical devices. Further, these methods and devices are not limited to surfaces favoring endothelial cell growth over smooth muscle cells. Surfaces helping to control (including differential growth, inhibition, cell guidance, apoptosis, etc.) of any appropriate cell type may be formed using the methods and systems described herein. The patterned surfaces described herein may also be referred to as nanostructured surfaces, nanostructured layers, or nanotextured surfaces.

One variations of the nanostructured surfaces descried herein includes patterned stent covers.

Method of Forming a Patterned Stent Cover

Figure 3:
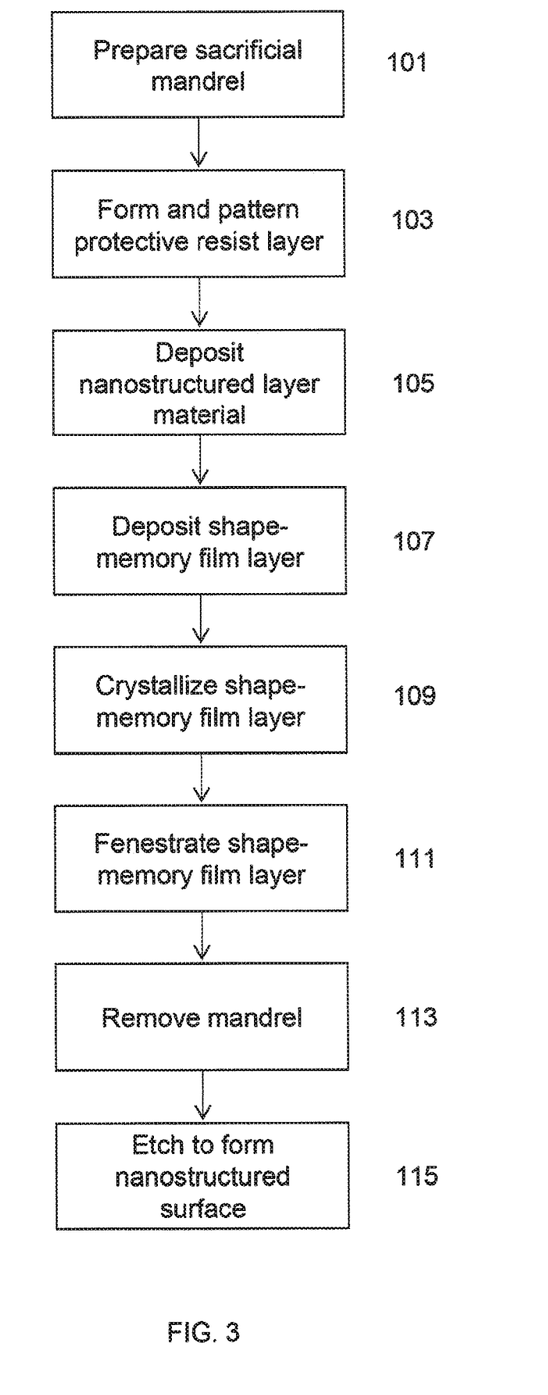
FIG. 3 is a schematic diagram illustrating one variation of a method for forming a stent cover, as described herein.

Referring to FIG. 3, a stent cover may be formed having a pattern preferential for adhesion of endothelial cells compared to smooth muscle cells.

The patterned stent covers described herein may be patterned in the appropriate size scale for preferential adhesion of endothelial cells. It is desired that the size be highly selective, providing a major advantage for endothelial cells to grow relative to smooth muscle cells. For example, the scale of the patterns described herein may be in the nanometer range (e.g., between 0.1 and 500 nm). It is believed that a regular pattern of 200 nm balls creates a surface that is selective for endothelial cells. (Derick C. Miller, Journal of Biomedical Materials Research, Part A, 81A, Issue 3, 678-684: cited in "Nanotechnology for Healing Damaged Vascular Tissues," Thomas Webster, www.scitizen.com/screens/blogPage/viewBlog/, last viewed Jul. 20, 2007).

A nanostructured surface may be formed as a layer created on the inside of the tubular stent cover by forming a protective pattern (e.g., by masking or otherwise protecting the material), then depositing a layer or layers of material that will form the nanostructural surface, and forming the outer shape memory material around the protective pattern and deposited layers. Once the shape memory material has been sufficiently prepared (e.g., crystallized), the mandrel may be removed, and the nanostructural surface may be formed by etching the pattern using microlithography to etch around the protected material of the protective pattern.

FIG. 3 describes one exemplary method for forming a stent cover having a nanostructural inner surface that is selective for endothelial cells over smooth muscle cells. In FIG. 3, a sacrificial mandrel is first prepared 101. In general, a sacrificial mandrel is a form that may be removed (e.g., by etching, erosion, etc.) once the layers of the stent cover have been formed around it. Thus, the sacrificial mandrel may be similar is shape and dimension to the outer surface of a stent with which the cover will be used. The material of the sacrificial mandrel is typically removable or etchable. For example, the sacrificial mandrel may be formed of copper. See, for example, U.S. Pat. No. 6,923,829 Boyle et al. These procedures are well known in MEMS technology.

A protective pattern may then be formed around the outside of the mandrel 103. As mentioned above, the protective pattern (or protective layer) at least partially forms the pattern of the nanostructure by selectively protecting the material forming the nanostructural surface from etching. For example, the protective pattern may be made from a thin layer of chromium, e.g., 10-100 nm thick, that is laid down on a cylindrical substrate 103 and formed into a desired pattern. The protective pattern may be formed by photolithographic techniques, as known in the art. For example, the chromium layer may be coated with a photoresist material and patterned by exposing it to negative (or positive) of at least a portion of the nanostructural layer followed by removal of the unexposed photoresist, etching to remove unprotected chromium, and removal of the photoresist layer. In one variation the chromium layer forms the shape and pattern of islets of the nanostructural surface. For example, the chrome layer may be patterned with a checkerboard design, so that the islets forming the nanostructure will be columnar islets having a square cross-section (see, e.g., FIGS. 4A-4C). After forming the protective pattern, the material forming the nanostructural surface layer may be applied over the protective pattern 105.

For example, alternating layers of material may be deposited over the protective pattern, as taught by Haushalter (U.S. Pat. No. 7,229,500). These layers may be referred to as sub-layers of the nanostructured surface, and will form the nanostructured surface. Any appropriate material may be layered on the protective pattern to form the nanostructured surface. In particular, materials may be chosen based on their potential for encouraging adhesion and/or growth of endothelial cells selectively, compared to smooth muscle cells. For example, the material may be a metal or alloy, including (but not limited to): Ti, TiNi, Au, Ni, Al, Fe, Pt, and Hf. Other materials having specific properties may be used, including those taught by Haushalter (U.S. Pat. No. 7,229,500). In some variations, the material is a doped material that includes a predetermined amount of some additional component. For example, the material forming a sub-layer of the nanostructured surface may be a metal or alloy that is doped with one or more transition elements, alkali (rare earth) metals, colloids, etc.

In some variations the layer of material forming the nanostructured surface includes a plurality of sub-layers of different materials. For example, the nanostructured surface may include repeated layers comprising two or more sub-layers. The material of each sub-layer may be different. The material properties of each sub-layer or layer may be different (e.g., hydrophobic/hydrophilic; +/−charge, etc.), in particular, there may be a difference in their rate of removal by a particular etchant. Thus, the materials forming the nanostructured surface may form one or more interfaces that can enhance attachment to endothelial cells, or inhibit attachment of smooth muscle cells. In some variations, the nanostructured surfaces include alternating sub-layers that may be differently etched to include recessed portions.

As mentioned, the sub-layers forming a nanosurface may be repeated. For example, a nanosurface may include a repeated motif of two or more sub-layers (e.g., sub-layer A and sub-layer B), that are repeated n times, so that the nanosurface comprises n layers of AB (or BA, depending on the order). The thickness of sub-layer A and sub-layer B may be uniform in each repeated layer, or the thicknesses may vary.

The dimensions of the nanostructured surface may be set by the combination of the pattern (e.g., the protective pattern), the thickness of the material(s) applied to form the nanostructured surface, and the etching used to form the nanostructural layer. In general, the nanostructured surface has dimensions that are within the nanometer scale (e.g., between 0.1 nm and 500 nm). For example, the nanostructured surface may be a repeated pattern of nanostructural "islets" having a predetermined depth (e.g., between 10 and 500 nm) and cross-sectional profile which matches the shapes formed of the protective pattern. For example, the islets may have square, rectangular, triangular, circular, oval, etc. shape. The predetermined depth of the islets may be determined by the thickness of the material(s) applied to the protective pattern on the mandrel (e.g., the thickness may be between 10 and 500 nm). The spacing between the islets may also be determined by the protective pattern (e.g., individual islets may be separated by between 10 and 500 nm, such as about 100 nm). In some variations, the nanostructure surface includes one or more wells etched to a shape and/or dimension as desired. For example, the wells may have a round, oveal, rectangular, or other shape, and may be between about 10 and 500 nm deep.

As mentioned, the shape, dimension and spacing of the islets/wells forming the nanostructure may be specifically chosen so that adhesion or growth of one cell type (e.g., endothelial cells) is favored in comparison to another cell type (e.g., smooth muscle cells). Thus, the shape, depth and arrangement of the islets/wells may be determined experimentally, as described in the examples below.

Returning now to FIG. 3, after the appropriate thickness of material forming the nanostructured surface has been applied 105, a layer of shape memory material is then applied 107. Any appropriate shape memory material may be used, particularly a shape memory alloy such as a nickel titanium alloy. One preferred material is Nitinol. The shape memory material is deposited as a thin film. When the desired thickness of thin film has been deposited, the material may then be heat-treated to crystallize 109. In some variations, the thin film layer shape memory material is then fenestrated (e.g., using standard MEMS photolithography). U.S. Pat. No. 6,533,905 to Johnson et al. describes one method of applying (e.g., by vacuum deposition including sputtering) a TiNi shape memory alloy as mentioned above, and a patterned stent cover may be made using some of the teachings described therein. For example, U.S. Pat. No. 6,533,905 may be exploited to make a tubular stent cover.

The thin layer of shape memory material may also be patterned. For example, the shape memory material may be fenestrated 111. Fenestrations may be biologically desirable (e.g., allowing access or in-growth).

The sacrificial substrate (e.g., the mandrel) may be removed, leaving a cylinder of thin film material (e.g., shape memory material) with a protective layer (e.g., chromium) and the layer(s) of materials that will form the nanostructured surface inside 113 the cylinder. The material forming the nanostructured layer(s) can be patterned by exposure to appropriate etchants 115.

The finished stent cover formed by the method of FIG. 3 is a fenestrated, tubular, thin film of shape memory material (e.g., Nitinol), inside of which is a surface consisting of nanostructures that have appropriately structures (e.g., layered islets) to selectively grow a layer of cell, including endothelial cells, preferentially to another type of cell, such as smooth muscle cells in the blood stream.

In general, materials (particularly the material or materials forming the nanostructured surface) must be selected for compatibility of the other steps of the method. For example, these materials must survive heat treatment without damage. Materials used must be compatible with deposition and processing of TiNi film, including crystallization at 500° C. Further, the etchants must be highly selective.

An assumption is made that there are different proteins in the cell membranes of smooth muscle cells than on endothelial cells. The experimental fact that endothelial cells grow preferentially on layers formed from spheres 200 nanometers in size appears to support this assumption (Thomas Webster, Nanotechnology for healing damaged vascular tissue, Nanomedicine Laboratories, Brown University, Providence R.I., www.scitizen.com).

A further assumption is that a repeating pattern of layers having an appropriate distance of repetition, each layer consisting of two or more sub-layers differing in some quality, will also act to enhance growth of endothelial cells. Since the appropriate distance is not known, it may be determined by experiment, as mentioned above. The examples below outline one method in which these parameters may be determined experimentally.

EXAMPLES

Optimizing a Nanoscale Pattern

As used here, the term "nanostructural pattern" may refer to a surface or layer having nanostructural features. In general, this is a surface having one or more repeated motifs of nanoscale structures. These nanoscale structures may be repeated "islets" etched from the one or more layers of material (or sub-layers) forming the nanostructural layer. Thus, the nanostructural layer may be a plurality of columnar islets separated from each other by a "street" or channel having a predetermined depth. A cross-section through an islet may be square, rectangular, circular, etc. The sides of an islet may present stratified layers made up of different materials, and the thickness (depth) of each layer (as well as the material from which the layer is made) may be chosen to select one type of cell over another type of cell (e.g., endothelial cells over smooth muscle cells). These islets may therefore present a larger surface area of interface boundaries between different materials which cells may contact. Certain cell types may preferentially adhere to some interface regions.

One or more nanostructural patterns that are selective for endothelial cells over smooth muscle cells may be determined experimentally using the methods and devices described herein. For example, U.S. Pat. No. 7,229,500 to Haushalter et al. describes a method of enhancing the crystallization of certain species of proteins by providing heterogeneous nucleation sites consisting of multiple nanometer scale thickness layers with alternating characteristics. The methods of the U.S. Pat. No. 7,229,500 patent may be adapted to form nanostructural patterns that may be tested to determine nanostructural layers (sub-layers) or patterns that preferentially support endothelial cells over smooth muscle cells. Nanometer scale, regular patterns of alternating layers and/or materials can be generated and systematically examined for interaction with both endothelial and smooth muscle cells, to determine which one or more regions of specific patterns may act as scaffolds for specific types of cell (e.g. endothelial cells) by causing their cell membrane proteins to adhere to the surface more strongly than other types of cells (e.g. smooth muscle cells). Successful application of this invention may result in a continuous layer of endothelial cells being formed on the surface of the stent cover.

Figures 4A, 4B:
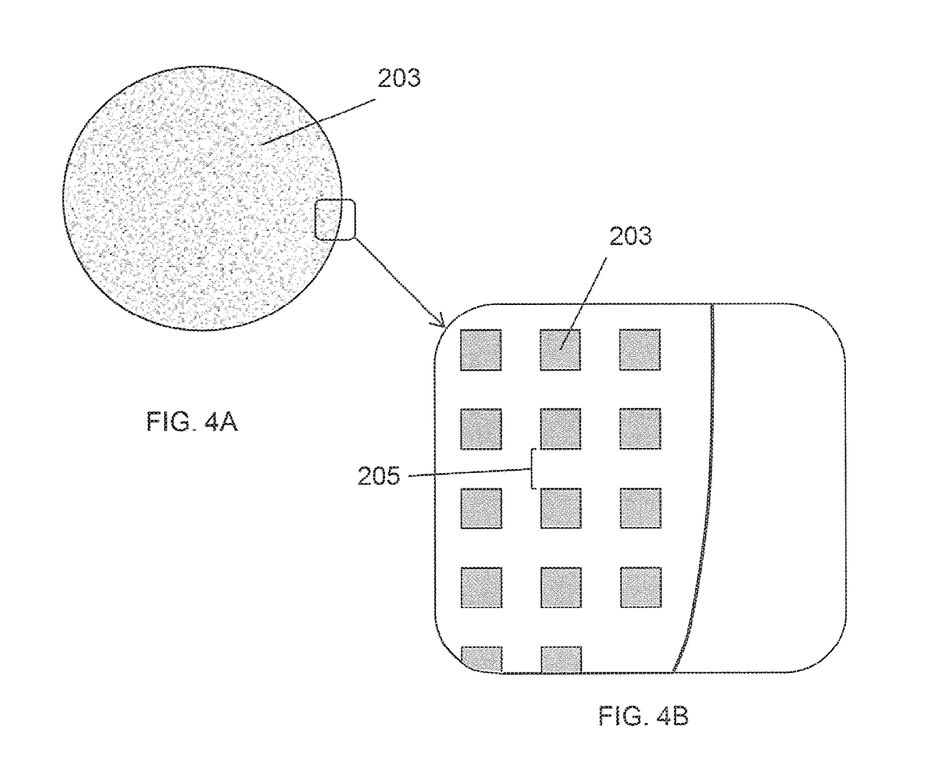
FIG. 4A is a test wafer on which a nanostructure has been formed.
FIG. 4B is a detailed view of a region of the wafer of FIG. 2A.
Figure 4C:
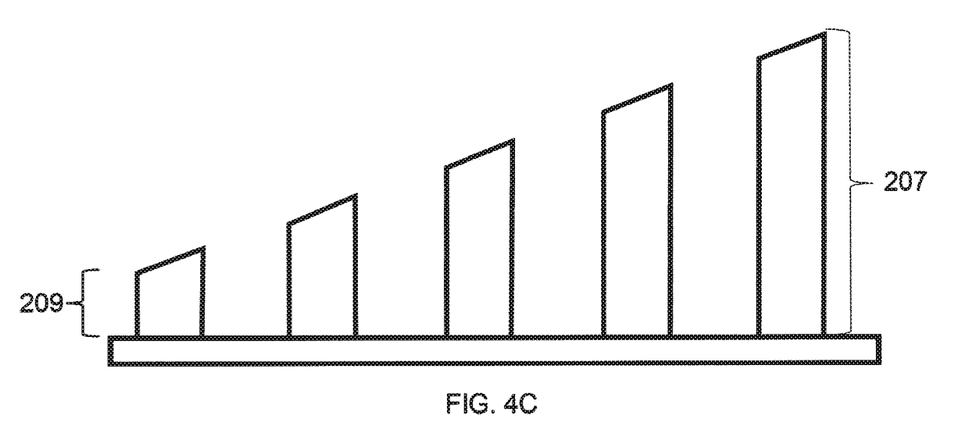
FIGS. 4C and 4D are cross-sectional views showing nanostructures.

In some variations, a library of different nanostructures (islets and/or wells) may be formed of layers of selected materials and thicknesses, so that the optimum thickness and materials can be determined to be selective for endothelial cells. FIGS. 4A-4C illustrates one variation of this. Initial experiments may be performed to determine whether endothelial cells can be separated from smooth muscle cells by graded thickness of metal on substrate. In one variation of this experiment, selectivity may be determined by varying the size scale.

Endothelial and smooth muscle cells may be grown on substrates with raised islets of graded varying thickness or with wells or depressions of various depths. The substrates may be inspected to see if cells grow preferentially on islets of a particular thickness and/or wells or a particular depth. The experiment may be performed by first preparing the substrate. In this example, the substrate is a wafer 201 onto which islets have been formed. The islets or wells (nanostructures) may be formed by sputter depositing one or more metal layers. The thickness of the metal layer may vary continuously from a few nanometers on one edge of wafer to about 500 nanometers on the other edge. After coating with layers of metal(s), the islets/wells may then be formed by patterning them by photolithography, and chemically milling them to produce regular patches or islets of metal, as shown in FIG. 4B, which is a close-up view of a region of the wafer 201 and 2C, which shows a cross-section through a wafer. In this example, islets 203 near one edge of the wafer are about 500 nm, and islets near other edge of the wafer are about 10 nm. Patterns in a particular region of a wafer may be kept uniform in length and width so that this is not a variable. For example, the cross-sectional shape of the islets on a particular wafer may be constant, even though the depth is varying. The size of islets may be varied from one wafer to another to test the effect of cross-sectional size. The cross-sectional shape (e.g., circular, polygonal—e.g., triangular, rectangular, square, etc.) may also be varied between wafers (or on a single wafer) to determine an effect. FIG. 4C illustrates a cross-section through a wafer (not to scale) showing exemplary islets having different thicknesses, e.g., from 10 nm (209) to 500 nm (207).

Different islet materials may also be tested. For example, different metals may be tested, including (but not limited to): Ti, TiNi, Au, Ni, Al, Fe, Pt, and Hf. In some variations, other materials may be used. In some variations, the layers of material may be doped with one or more molecules. For example, there are known cell-adhesion proteins that may be incorporated as part of the layered material. Other materials include transition elements, alkali or alkaline/rare earth materials, oxyacids, nitrates, acetates, sulfates, colloids, etc.

To test, pairs of wafers may be exposed to two different cell types, or a single wafer may be exposed to two different cell types (e.g., the wafer may be divided in half). For example, one wafer (or half a wafer) may be exposed to endothelial cells, while the other wafer (or half of the wafer) is exposed to smooth muscle cells. After an appropriate time, the wafers may be inspected to determine if there is a significant difference in the way the two types of cells adhere and/or grow. This method may help answer the question as to whether cells grow preferentially on a specific thickness of material, as well as which materials may be preferred. In particular, this type of experiment may help determine if there is a thickness and/or material to which endothelial cells adhere or grow better than smooth muscle cells.

The test wafers described herein may be formed on a glass substrate. For example, a 4-inch wafer having an oxidized surface (to present a smooth glass surface) may be used. A pair of wafers may each be identically deposited with the metal (or other material) in a thickness gradient from one side of the wafer to the other. For example, the thickness may be varied from 500 to 10 nanometers. Afterwards, the islets and/or wells may be patterned. In one variation, three patterns of islets/wells (having different cross-sectional sizes) may be formed per wafer. For example, a square profile islet having a length and width of 1 mm, 0.5 mm, or 0.1 mm may be formed on each wafer. The spacing between each islet (the street) may be about 100 nm wide. The islets may be patterned by photolithography using a prepared mask exposed to the coated surface of the wafer after applying a layer of photoresist. The exposed photoresist may then be removed, and the wafer etched. Afterwards, the wafer (including the formed islets) may be cleaned to remove all chemicals (etchant, etc.) from the wafer.

Cell growth or adhesion on the wafers may be tested in any appropriate way. For example, cell growth may be examined after incubating with cells or after exposing to flows of cells. Wafers can then be examined for successful growth, especially growth at a particular metal thickness. Statistics (cell counts, etc.) may be taken to quantify any effects.

Figure 4D:
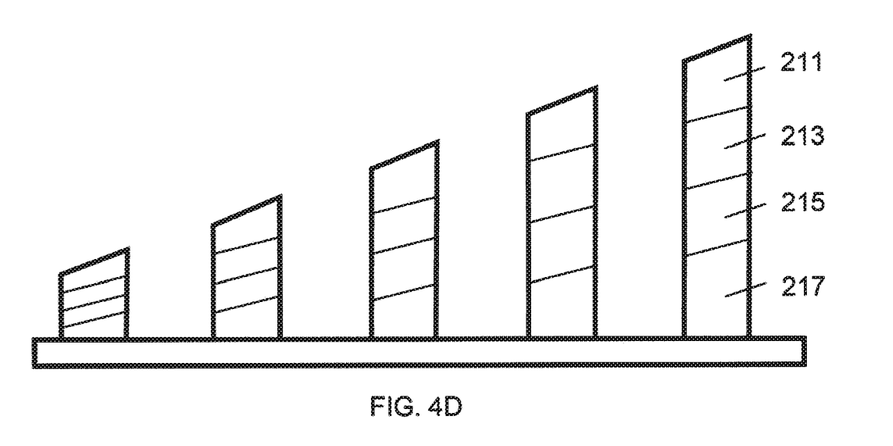

The sensitivity of these experiments may be enhanced as part of a second phase of experiments. Selectivity can be increased by making nanostructures (e.g., islets, wells, etc.) having multiple layers, as shown in FIG. 4D. Different materials may be layered onto the wafer in alternating layers 211, 213, 215, 217. Materials having contrasting properties (e.g., hydrophilic/hydrophobic, charged/uncharged, +/−charges, doped/undoped, and/or different etching rates) may be of particular interest. Multiple-layered islets/wells may be formed similar to the method just described above, and similarly tested. In addition to tests against isolated cells, materials may be tested in an animal model. For example, rather than using a glass wafer as the test substrate, the substrate may be a nickel-titanium material. Thus, a testing stent or stent cover may be formed having varying characteristics for the nanostructures, as briefly described above, and implanted into an animal model for testing. This test stent cover or stent may be retrieved after an appropriate time, and histologically examined to determine which regions (corresponding to which nanostructures) had desirable properties with respect to endothelial versus smooth muscle cells.

The nanostructured layer may be formed of multiple layers or sub-layers of material, as described above and illustrated in FIG. 4D. In some variations, the nanostructured surface may be formed of multiple repeated sub-layers. For example, two layers can be repeated to form a layer that may be etched to form the nanostructured surface. The thicknesses of the two sub-layers may be varied in two gradients across the surface of the substrate. For example, the thickness of the first sub-layer can decrease from the left to the right of the substrate. The thickness of the second sub-layer can decrease from the back to the front of the substrate. The overall thickness of the nanostructured surface (the depth of each islet) may be kept approximately constant across the substrate (e.g., by increasing the number of layers applied). This substrate may be used to test the effect of the thicknesses of each sub-layer on cell adhesion and growth, as described above.

Figure 4E:
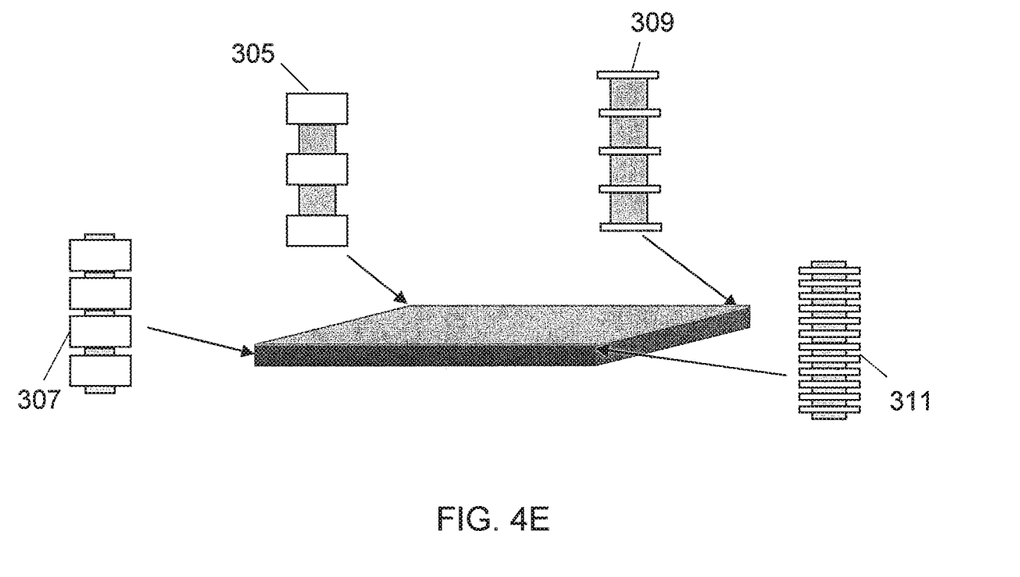
FIG. 4E shows cross-sectional views of a nanostructured substrate in accordance with an embodiment of the disclosure.

In addition to the thickness of the nanostructure-forming layer(s), the shape of the nanostructure(s) may also be varied. Differential etching may be used to form a superlattice having different interlayer spacing. For example, one or the sub-layers forming the nanostructured surface may be etched more than the other sub-layer(s), as shown in FIG. 4E. In FIG. 4E, the second (grey) sublayers etches more than the first (white) sublayers. This results in a nanotextured 3-D surfaces in which one of the sub-layers is undercut compared to the other sub-layer, forming indentations, pockets, ledges and/or terraces along the surface, as shown in FIG. 4E 305, 307, 309, and 311. The amount of relative etching of each sub-layer can also be varied to determine the effect on cell adhesion and growth, as described above. For example, by varying the etching times and/or etch rates, different amounts of surface etching may be achieved.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:
1. A thin-film stent cover comprising: the thin film stent cover applied to a surface of a stent, wherein the thin film stent cover comprising:
   a plurality of layers comprising a first layer of a first metal material, a second layer of the first metal material, and a third layer of a second metal material different from the first metal material, the third layer disposed between the first and the second layers; and a plurality of fenestrations, each fenestration formed through the plurality of layers by microlithography etching a first opening in the first layer, a second opening in the second layer and a third opening in the third layer, the first, second, and third openings are aligned to form a continuous fenestration through the plurality of layers, wherein the second metal material has a material property of a greater etch rate than the first metal material such that the third opening of the third layer is etched to be greater in size than a size of each of the first and second openings of the first and second layers by differential etching to form a recess between the first and second openings of the first and second layers within the continuous fenestration, wherein a thickness of at least one of the plurality of layers is varied in a gradient across a surface of the at least one of the plurality of layers, wherein the plurality of fenestrations form a nanostructural surface configured so that one type of cells preferentially adhere to the nanostructural surface as compared to another type of cells and/or the nanostructural surface is configured to facilitate adherence of cells to the nanostructural surface as compared to a surface without the nanostructural surface, and wherein each of the fenestrations has a size of between about 10 microns and about 400 microns.

2. The thin-film stent cover of claim 1, wherein one of the first and the second metal materials comprises titanium alloy and the other of the first and second metal materials comprises nickel-titanium alloy.

3. The thin-film stent cover of claim 1, wherein the first metal material and/or the second metal material comprise a metal selected from the group consisting of: Ti, TiNi, Au, Ni, Al, Fe, Pt, and Hf.

4. A thin-film stent cover comprising: the thin film stent cover applied to a surface of a stent, wherein the thin film stent cover comprising:

a plurality of layers comprising a first layer of a first metal material, a second layer of the first metal material, and a third layer of a second metal material different from the first metal material, the third layer disposed between the first and the second layers; and a plurality of wells, each well extending through at least a subset of the plurality of layers by microlithography etching a first opening in the first layer, a second opening in the second layer and a third opening in the third layer, the first, second, and third openings are aligned to form a continuous well through the subset of the plurality of layers, wherein the second metal material has a material property of a greater etch rate than the first metal material such that the third opening of the third layer is etched to be greater in size than a size of each of the first and second openings of the first and second layers by differential etching to form a recess between the first and second openings of the first and second layers within the continuous well, wherein a thickness of at least one of the plurality of layers is varied in a gradient across a surface of the at least one of the plurality of layers, wherein the plurality of wells form a nanostructural surface configured so that one type of cells preferentially adhere to the nanostructural surface as compared to another type of cells and/or the nanostructural surface is configured to facilitate adherence of cells to the nanostructural surface as compared to a surface without the nanostructural surface, and wherein the wells have a depth of between about 10 nm and about 500 nm.

5. The thin-film stent cover of claim 4, wherein one of the first and the second metal materials comprises titanium alloy and the other of the first and second metal materials comprises nickel-titanium alloy.

6. The thin-film stent cover of claim 4, wherein the first metal material and/or the second metal material comprise a metal selected from the group consisting of: Ti, TiNi, Au, Ni, Al, Fe, Pt, and Hf.

7. A thin-film stent cover comprising: the thin film stent cover applied to a surface of a stent, wherein the thin film stent cover comprising:

a plurality of layers comprising a first layer of a first metal material, a second layer of the first metal material, and a third layer of a second metal material different from the first metal material, the third layer disposed between the first and the second layers; and a plurality of raised islets, each raised islet formed by microlithography etching of a subset of the plurality of layers to form a first step in the first layer, a second step in the second layer and a third step in the third layer, the first, second, and third steps are aligned in a stack to form a raised islet;

wherein the second metal material has a material property of a greater etch rate than the first metal material such that the third step of the third layer is etched to be smaller in size than a size of each of the first and second steps of the first and second layers by differential etching to form a recessed third step between the first and second steps of the first and second layers around the raised islet, wherein a thickness of at least one of the plurality of layers is varied in a gradient across a surface of the at least one of the plurality of layers, wherein the plurality of islets form a nanostructural surface configured so that one type of cells preferentially adhere to the nanostructural surface as compared to another type of cells and/or the nanostructural surface is configured to facilitate adherence of cells to the nanostructural surface as compared to a surface without the nanostructural surface, and wherein the raised islets have a thickness of between about 10 nm and about 500 nm.

8. The thin-film stent cover of claim 7, wherein one of the first and the second metal materials comprises titanium alloy and the other of the first and second metal materials comprises a nickel-titanium alloy.

9. The thin-film stent cover of claim 7, wherein the first metal material and/or the second metal material comprise a metal selected from the group consisting of: Ti, TiNi, Au, Ni, Al, Fe, Pt, and Hf.

* * * * *